United States Patent
Wegmann et al.

(10) Patent No.: US 9,215,874 B2
(45) Date of Patent: Dec. 22, 2015

(54) FUNGICIDAL COMPOSITION COMPRISING A PYRIDYLMETHYLBENZAMIDE DERIVATIVE AND A THIAZOLECARBOXAMIDE DERIVATIVE

(76) Inventors: Thomas Wegmann, Langenfeld (DE); Jean-Marie Gouot, Saint Cyr au Mont d'Or (FR); Marie-Pascale Latorse, Saint Romain de Popey (FR)

(\*) Notice: Subject to any disclaimer, the term of this patent is extended or adjusted under 35 U.S.C. 154(b) by 1386 days.

(21) Appl. No.: 11/884,154

(22) PCT Filed: Feb. 9, 2006

(86) PCT No.: PCT/EP2006/002580
§ 371 (c)(1),
(2), (4) Date: Dec. 11, 2007

(87) PCT Pub. No.: WO2006/084773
PCT Pub. Date: Aug. 17, 2006

(65) Prior Publication Data
US 2008/0214624 A1 Sep. 4, 2008

(30) Foreign Application Priority Data
Feb. 11, 2005 (EP) .................................. 05356032

(51) Int. Cl.
*A01N 43/78* (2006.01)
(52) U.S. Cl.
CPC .................................. *A01N 43/78* (2013.01)
(58) Field of Classification Search
CPC .................................................. A01N 43/78
See application file for complete search history.

(56) References Cited

U.S. PATENT DOCUMENTS

| | | | | |
|---|---|---|---|---|
| 6,015,802 A | * | 1/2000 | Duvert | 514/141 |
| 7,601,673 B2 | * | 10/2009 | Blasco et al. | 504/116.1 |
| 2008/0039319 A1 | * | 2/2008 | Blettner et al. | 504/100 |

FOREIGN PATENT DOCUMENTS

| | | | | |
|---|---|---|---|---|
| EP | 0639574 | * | 8/1994 | ........... C07D 417/12 |
| EP | 0 639 574 | | 2/1995 | |
| GB | WO99/42447 | * | 8/1999 | ........... C07D 213/61 |
| WO | WO 02/069712 | | 9/2002 | |
| WO | WO 03/041501 | | 5/2003 | |
| WO | WO 03/079788 | | 10/2003 | |

OTHER PUBLICATIONS

Theodore Cohen & Gary Deets, Trapping of Picolyl Cations in the Reactions of 2- and 4-picoline n-Oxide with Acetic Anhydride, 94 JACS 932 (1972).*
Ra C. S., et al. "Synthesis and Fungicidal Activity of Novel 2-Aminothiazole Carboxamide Derivatives", Korean Journal of Medicinal Chemistry Korean Chemical Society, Seoul, KR, vol. 5, No. 2, 1995, pp. 72-75, XP000944804, ISSN: 1225-0058.
D.-S. Kim et al.: Synthesis and Fungicidal Activity of Ethaboxam Against Oomycetes, Pest Management Science, vol. 60, No. 10, 2004, pp. 1007-1012, XP002332654, abstract.

\* cited by examiner

*Primary Examiner* — Sean Basquill
(74) *Attorney, Agent, or Firm* — Ostrolenk Faber LLP

(57) ABSTRACT

A composition comprising at least a pyridylmethylbenzamide derivative of general formula (1)

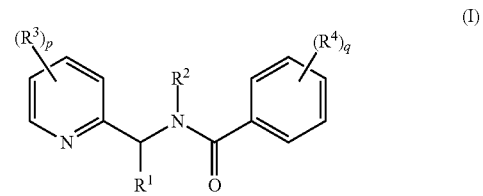

and N-(cyano-2-thienylmethyl)-4-ethyl-2-(ethylamino)-5-thiazolecarboxamide; in an (a)/(b) weight ratio of from 0.01 to 10.
A composition further comprising an additional fungicidal compound.
A method for preventively or curatively combating the phytopathogenic fungi of crops by using this composition.

7 Claims, No Drawings

FUNGICIDAL COMPOSITION COMPRISING A PYRIDYLMETHYLBENZAMIDE DERIVATIVE AND A THIAZOLECARBOXAMIDE DERIVATIVE

The present application is a 35 U.S.C. §371 national phase conversion of PCT/EP2006/002580 filed Feb. 9, 2006, which claims priority of European Application No. 05356032.2 filed Feb. 11, 2005.

The present invention relates to novel fungicidal compositions comprising a pyridylmethylbenzamide derivative and a thiazolecarboxamide derivative. The present invention also relates to a method of combating phytopathogenic fungi by applying at a locus infested or liable to be infested such a composition.

European patent application EP-A-1056723 generically discloses the possibility of combining pyridylmethybenzamide derivatives with known fungicidal products to develop a fungicidal activity.

International patent application WO 02/069713 discloses fungicidal mixtures comprising a pyridylmethylbenzamide derivative and phosphorous acid or one of its derivatives.

International patent application WO 2004/079788 discloses numerous fungicidal mixtures comprising a pyridylmethybenzamide derivative and an other fungicide active ingredient. Thiazolecarboxamide derivatives are not cited as potential partners of pyridylmethylbenzamide derivatives.

Some of the above mentioned mixtures have shown a synergistic effect. Nevertheless, it is always of high-interest in agriculture to use novel pesticidal mixtures showing a synergistic effect in order to avoid or to control the development of resistant strains to the active ingredients or to the mixtures of known active ingredients used by the farmer while minimising the doses of chemical products spread in the environment and reducing the cost of the treatment.

We have now found some novel fungicidal compositions which possess the above mentioned characteristics.

Accordingly, the present invention relates to a composition comprising:
a) a pyridylmethylbenzamide derivative of general formula (I)

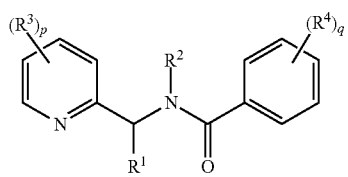

in which:
R$^1$ may be a hydrogen atom, an optionally substituted alkyl group or an optionally substituted acyl group;
R$^2$ may be a hydrogen atom or an optionally substituted alkyl group;
R$^3$ and R$^4$ may be chosen independently from each other as being a halogen atom, a hydroxyl group, a cyano group, a nitro group, —SF$_5$, a trialkylsilyl group, an optionally substituted amino group, an acyl group, or a group E, OE or SE, in which E may be an alkyl, alkenyl, alkynyl, cycloalkyl, cycloalkenyl, aryl or a heterocyclyl group each of which may optionally be substituted;
p represents 0, 1, 2, 3 or 4;
q represents 0, 1, 2, 3 or 4;
and its agriculturally acceptable optical and/or geometric isomers, tautomers and addition salts with an acid or a base; and
b) N-(cyano-2-thienylmethyl)-4-ethyl-2-(ethylamino)-5-thiazolecarboxamide;
in a (a)/(b) weight ratio of from 0.01 to 10.

N-(cyano-2-thienylmethyl)-4-ethyl-2-(ethylamino)-5-thiazolecarboxamide is a thiazolecarboxamide derivative fungicide also known as ethaboxam.

In the context of the present invention:
the term halogen means bromine, chlorine, iodine or fluorine;
the term alkyl means a linear or branched saturated hydrocarbon group containing from 1 to 6 carbon atoms;
the term alkenyl means a linear or branched hydrocarbon group containing from 2 to 6 carbon atoms and an unsaturation in the form of double bond;
the term alkynyl means a linear or branched hydrocarbon group containing from 2 to 6 carbon atoms and an unsaturation in the form of a triple bond;
the term alkoxy means a linear or branched alkyloxy group containing from to 1 to 6 carbon atoms;
the term acyl means a formyl group or linear or branched alkoxycarbonyl group containing from 2 to 6 carbon atoms;
the term cycloalkyl means a saturated cyclic hydrocarbon group containing from 3 to 8 carbon atoms;
the term aryl means a phenyl or naphthyl group;
the term heterocyclyl means saturated, partially saturated, unsaturated or aromatic cyclic group containing from 3 to 8 atoms, which may be a carbon atom, a nitrogen atom, a sulphur atom or an oxygen atom. Examples of such heterocyclyl may be pyridyl, pyridinyl, quinolyl, furyl, thienyl, pyrrolyl, oxazolinyl;
the term "optionally substituted" means that the group thus termed may be substituted with one or more groups which may be halogen, alkyl, alkoxy, hydroxyl, nitro, amino, cyano or acyl.

The composition according to the present invention provides a synergistic effect. This synergistic effect allows a reduction of the chemical substances spread into the environment and a reduction of the cost of the fungal treatment.

In the context of the present invention, the term "synergistic effect" is defined by Colby according to the article entitled "Calculation of the synergistic and antagonistic responses of herbicide combinations" Weeds, (1967), 15, pages 20-22.

The latter article mentions the formula:

$$E = x + y - \frac{x*y}{100}$$

in which E represents the expected percentage of inhibition of the disease for the combination of the two fungicides at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition observed for the combination is greater than E, there is a synergistic effect.

The composition according to the present invention comprises a pyridylmethylbenzamide derivative of general formula (I).

Preferably, the present invention relates to a composition comprising a pyridylmethylbenzamide derivative of general formula (I) in which the different characteristics may be chosen alone or in combination as being:

as regards $R^1$ and $R^2$, $R^1$ and $R^2$ may be chosen independently from each other as being a hydrogen atom or an optionally substituted alkyl group. More preferably, $R^1$ and $R^2$ may be chosen independently from each other as being a hydrogen atom, a methyl group or an ethyl group. Even more preferably, $R^1$ and $R^2$ may be both hydrogen atoms.

as regards $R^3$ and $R^4$, $R^3$ and $R^4$ may be chosen independently from each other as being a halogen atom, a hydroxyl group, a nitro group, an optionally substituted amino group, an acyl group, or a group E, OE or SE, in which E may be a alkyl, a cycloalkyl, a phenyl or a heterocyclyl group, each of which may optionally be substituted. More preferably, $R^3$ and $R^4$ may be chosen independently from each other as being a halogen atom, a nitro group or a halogenalkyl group. Even more preferably $R^3$ and $R^4$ may be chosen independently from each other as being a chlorine atom, a nitro group or a trifluoromethyl group.

as regards p, p may be 1 or 2. More preferably, p may be 2.

as regards q, q may be 1 or 2. More preferably, q may be 2;

and its agriculturally acceptable possible tautomers and addition salts with an acid or a base.

More preferably, the pyridylmethylbenzamide derivative of general formula (I) present in the composition of the present invention is:

a compound (Ia) which is 2,6-dichloro-N-{[3-chloro-5-(trifluoromethyl)-2-pyridinyl]methyl}benzamide; or a compound (Ib) which is N-{[3-chloro-5-(trifluoromethyl)-2-pyridinyl]methyl}-2-fluoro-6-nitrobenzamide; or a compound (Ic) which is N-{[3-chloro-5-(trifluoromethyl)-2-pyridinyl]methyl}-2-methyl-6-nitrobenzamide;

and its agriculturally acceptable possible tautomers and addition salts with an acid or a base.

The composition according to the present invention comprises at least a pyridylmethylbenzamide derivative of general formula (I) (a) and dithianon (b) in an (a)/(b) weight ratio of from 0.01 to 10; preferably of from 0.05 to 5; even more preferably, of from 0.1 to 1.

The composition of the present invention may further comprise a third fungicide active ingredient (c).

The fungicidal active ingredient (c) may be selected from azaconazole, azoxystrobin, (Z)-N-[α-(cyclopropylmethoxyimino)-2,3-difluoro-6-(trifluoromethyl)benzyl]-2-phenylacetamide, (RS)-2-(4-chlorophenyl)-N-[3-methoxy-4-(prop-2-ynyloxy)phenethyl]-2-(prop-2-ynyloxy)acetamide, benalaxyl, benomyl, benthiavalicarb, biphenyl, bitertanol, blasticidin-S, boscalid, borax, bromuconazole, bupirimate, sec-butylamine, calcium polysulfide, captafol, captan, carbendazim, carboxin, carpropamid, chinomethionat, chlorothalonil, chlozolinate, copper hydroxide, copper octanoate, copper oxychloride, copper sulfate, cuprous oxide, cymoxanil, cyproconazole, cyprodinil, dazomet, debacarb, dichlofluanid, dichlorophen, diclocymet, diclomezine, dicloran, diethofencarb, difenoconazole, difenzoquat metilsulfate, difenzoquat, diflumetorim, dimethirimol, dimethomorph, diniconazole, dinobuton, dinocap, diphenylamine, dithianon, dodemorph, dodemorph acetate, dodine, edifenphos, epoxiconazole, ethirimol, ethoxyquin, etridiazole, famoxadone, fenamidone, fenarimol, fenbuconazole, fenfuram, fenhexamid, fenpiclonil, fenoxanil, fenpropidin, fenpropimorph, fentin, fentin hydroxide, fentin acetate, ferbam, ferimzone, fluazinam, fludioxonil, fluoroimide, fluoxastrobin, fluquinconazole, flusilazole, flusulfamide, flutolanil, flutriafol, folpet, formaldehyde, fosetyl, fosetyl-aluminium, fosetyl-sodium, fuberidazole, furalaxyl, furametpyr, guazatine, guazatine acetates, hexachlorobenzene, hexaconazole, 8-hydroxyquinoline sulfate, potassium hydroxyquinoline sulfate, hymexazol, cyazofamid, imazalil sulfate, imazalil, imibenconazole, iminoctadine, iminoctadine triacetate, ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, metalaxyl-M, metam-sodium, metam, metconazole, methasulfocarb, methyl isothiocyanate, metiram, metominostrobin, mildiomycin, myclobutanil, nabam, nickel bis(dimethyldithiocarbamate), nitrothal-isopropyl, nuarimol, octhilinone, ofurace, oleic acid, oxadixyl, oxine-copper, oxpoconazole fumarate, oxycarboxin, pefurazoate, penconazole, pencycuron, pentachlorophenol, sodium pentachlorophenoxide, pentachlorophenyl laurate, phenylmercury acetate, sodium 2-phenylphenoxide, 2-phenylphenol, phthalide, picoxystrobin, piperalin, polyoxinspolyoxin B, polyoxin, polyoxorim, probenazole, prochloraz, procymidone, propamocarb hydrochloride, propamocarb, propiconazole, propineb, prothioconazole, pyrazophos, pyributicarb, pyrifenox, pyrimethanil, pyroquilon, quinoxyfen, quintozene, silthiofam, spiroxamine, sulfur, tar oils, tebuconazole, tecnazene, tetraconazole, thiabendazole, thifluzamide, thiophanate-methyl, thiram, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, phosphorous acid, pyraclostrobin and simeconazole.

The third fungicidal active ingredient may preferably be selected from phosphorous acid derivative, phosphorous acid itself, or alkali metal, alkaline-earth metal or metallic salts thereof. More preferably, the additional fungicidal compound may be chosen as being fosetyl-aluminium.

Where the third active ingredient (c) as defined above is present in the composition, this compound may be present in an amount of (a):(b):(c) weight ratio of from 0.01:1:1 to 10:1:30; the ratios of compound (a) and compound (c) varying independently from each other. Preferably, the (a):(b):(c) weight ratio may be of from 0.05:1:2 to 5:1:25; more preferably of from 0.1:1:3 to 1:1:20; the ratios of compound (a) and compound (c) varying independently from each other.

Following compositions may be cited to illustrate in a non-limited manner the present invention: compound (Ia) with ethaboxam; compound (Ia) with ethaboxam and fosetyl-aluminium; compound (Ib) with ethaboxam; compound (Ib) with ethaboxam and fosetyl-aluminium; compound (Ic) with ethaboxam; compound (Ic) with ethaboxam and fosetyl-aluminium.

The composition according to the present invention may further comprise an other additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The fungicidal compositions of the present invention can be used to curatively or preventively control the phytopathogenic fungi of crops. Thus, according to a further aspect of the present invention, there is provided a method for preventively or curatively controlling phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., Actinidaceae sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the present invention, mention may be made of:

Powdery mildew diseases such as:

*Blumeria* diseases, caused for example by *Blumeria graminis;*

*Podosphaera* diseases, caused for example by *Podosphaera leucotricha,*

*Sphaerotheca* diseases, caused for example by *Sphaerotheca fuliginea;*

*Uncinula* diseases, caused for example by *Uncinula necator;*

Rust diseases such as:

*Gymnosporangium* diseases, caused for example by *Gymnosporangium sabinae;*

*Hemileia* diseases, caused for example by *Hemileia vastatrix;*

*Phakopsora* diseases, caused for example by *Phakopsora pachyrhizi* or *Phakopsora meibomiae;*

*Puccinia* diseases, caused for example by *Puccinia recondita;*

*Uromyces* diseases, caused for example by *Uromyces appendiculatus;*

Oomycete diseases such as:

*Bremia* diseases, caused for example by *Bremia lactucae;*

*Peronospora* diseases, caused for example by *Peronospora pisi* or *P. brassicae;*

*Phytophthora* diseases, caused for example by *Phytophthora infestans;*

*Plasmopara* diseases, caused for example by *Plasmopara viticola;*

*Pseudoperonospora* diseases, caused for example by *Pseudoperonospora humuli* or *Pseudoperonospora cubensis;*

*Pythium* diseases, caused for example by *Pythium ultimum*;
Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus*,
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola*; *Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*;
*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incarnata*;
*Venturia* diseases, caused for example by *Venturia inaequalis*;
Root and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;
Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;
Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases:
*Fusarium* diseases, caused for example by *Fusarium culmorum*;
*Phytophthora* diseases, caused for example by *Phytophthora cactorum*;
*Pythium* diseases, caused for example by *Pythium ultimum*;
*Rhizoctonia* diseases, caused for example by *Rhizoctonia solani*;
*Sclerotium* diseases, caused for example by *Sclerotium rolfsii*;
*Microdochium* diseases, caused for example by *Microdochium nivale*,
Canker, broom and dieback diseases such as:
*Nectria* diseases, caused for example by *Nectria galligena*;
Blight diseases such as:
*Monilinia* diseases, caused for example by *Monilinia laxa*;
Leaf blister or leaf curl diseases such as:
*Taphrina* diseases, caused for example by *Taphrina deformans*;
Decline diseases of wooden plants such as:
*Esca* diseases, caused for example by *Phaemoniella clamydospora*;
Diseases of flowers and Seeds such as:
*Botrytis* diseases, caused for example by *Botrytis cinerea*;
Diseases of tubers such as:
*Rhizoctonia* diseases, caused for example by *Rhizoctonia solani*.

The fungicidal composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 2000 g/ha, preferably between 50 and 1500 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used fore the preparation of composition useful to curatively or preventively treat human and animal fungal diseases such as, for example, mycoses, dermatoses, trichophyton diseases and candidiases or diseases caused by *Aspergillus* spp., for example *Aspergillus fumigatus*.

The invention claimed is:
1. A composition comprising:
   a) 2,6-dichloro-N-{[3 chloro-5-(trifluoromethyl)-2-pyridinyl]methyl}-benzamide and its agriculturally acceptable optical and/or geometric isomers, tautomers and addition salts with an acid or a base; and
   b) N-(cyano-2-thienylmethyl-4-ethyl-2-(ethyl amino)-5-thiazolecarboxamide; in an a)/b) weight ratio of from 1 to 1.5.
2. The composition of claim 1 further comprising a fungicidal compound c).
3. The composition of claim 1 further comprising an agriculturally acceptable support, carrier, filler and/or surfactant.
4. A method for controlling phytopathogenic fungi of crops comprising applying an effective and non-phytotoxic amount of a composition of claim 1 to the seed, the plant and/or to the fruit of the plant or to the soil in which the plant is growing or in which it is desired to grow.
5. The method of claim 4 wherein the plant is a vine.
6. The composition of claim 2 wherein the fungicidal compound c) is fosetyl-aluminum.
7. The composition of claim 2 wherein the a)/b)/c) weight ratio is 1:1:1 to 1:1.5:30, the ratios of compound a) and compound c) varying independently from each other.

* * * * *